(12) United States Patent
Takahara et al.

(10) Patent No.: US 6,623,159 B2
(45) Date of Patent: Sep. 23, 2003

(54) METHOD FOR ANALYZING THERMAL DEFORMATION

(75) Inventors: Tadayoshi Takahara, Aichi-ken (JP); Jun Chen, Toyota (JP); Yoshio Sugimoto, Yokosuka (JP)

(73) Assignees: Toyota Jidosha Kabushiki Kaisha, Toyota (JP); Kanto Jidosha Kogyo Kabushiki Kaisha, Yokosuka (JP)

( * ) Notice: Subject to any disclaimer, the term of this patent is extended or adjusted under 35 U.S.C. 154(b) by 20 days.

(21) Appl. No.: 09/942,876

(22) Filed: Aug. 31, 2001

(65) Prior Publication Data

US 2003/0053515 A1 Mar. 20, 2003

(51) Int. Cl.$^7$ .............................................. G01N 25/16
(52) U.S. Cl. ...................................................... 374/55
(58) Field of Search ................................. 374/55, 57, 5

(56) References Cited

U.S. PATENT DOCUMENTS

| 4,237,089 A | 12/1980 | Kubat et al. ............. 264/328.1 |
| 5,048,346 A | * 9/1991 | Yano et al. .................... 374/57 |
| 2002/0021452 A1 | 2/2002 | Suresh et al. ............... 356/521 |

FOREIGN PATENT DOCUMENTS

| DE | 4211131 A1 | * 10/1993 | ................... 374/55 |
| JP | 54011787 A | * 1/1979 | ................... 374/55 |
| JP | 59171843 A | * 9/1984 | ................... 374/55 |
| JP | 03140836 A | * 6/1991 | ................... 374/57 |
| JP | 04353751 A | * 12/1992 | ................... 374/55 |
| JP | 04366744 A | * 12/1992 | ................... 374/55 |
| JP | 11-166884 | 6/1999 | |
| JP | 2001153827 A | * 6/2001 | ................... G01N/25/16 |

\* cited by examiner

Primary Examiner—Diego Gutierrez
Assistant Examiner—Mirellys Jagan
(74) Attorney, Agent, or Firm—Burns, Doane, Swecker & Mathis, LLP

(57) ABSTRACT

In order to precisely analyze thermal deformation of a substance which thermally shrinks over time, the amount of deformation of a substance is determined by separate steps of calculation of elasto-plastic deformation during temperature increase (step S12); calculation of creep deformation from the time when the temperature increase is completed till the time when the temperature decrease is started (step S14); and calculation of elasto-plastic deformation during the temperature decrease (step S16). When calculating the creep deformation, it is assumed that deformation due to the thermal shrinkage of the substance over time occurs simultaneous with the creep deformation, and strain rate is calculated as the time derivative of the total strain which is the sum of creep strain and the strain produced by thermal shrinkage. The creep deformation is then calculated by integrating the strain rate over the time from when the temperature increase is completed until the time when the temperature decrease is started.

4 Claims, 8 Drawing Sheets

METHOD FOR ANALYZING THERMAL DEFORMATION

BACKGROUND OF THE INVENTION

1. Field of the Invention

The present invention relates to a method for analyzing thermal deformation, and in particular to a thermal deformation analyzing method for analyzing thermal deformation of a substance in response to temperature increase or decrease, and as time elapses during a temperature increase or decrease.

2. Description of the Related Art

Conventionally, a method for analyzing the structure of a substance (for example, a plastic molded part) has been proposed in which stress of the substance is analyzed based on the material data such as the linear expansion coefficient, Young's modulus, and Poisson's ratio of the substance, the shape and constraint condition of the substance, and, at the same time, the creep strain generated in response to the stress occurring on the substance is analyzed using Nutting's formula shown as Equation (1) An example of analysis software is that marketed under the trade name ABAQUS.

$$\frac{\partial \varepsilon}{\partial t} = A\sigma^n t^m \qquad (1)$$

However, in such an analyzing method, because the tensile creep characteristic is used as the creep characteristic when the substance is bent (referred to as the bending creep characteristic hereinafter), there is a problem that the precision of the analysis of the bending creep characteristic is low. Also, because thermal shrinkage which occurs as time elapses is not considered, there is an additional problem that for a substance having a thermal shrinkage characteristic, the conventional method may result in large error.

In order to solve the problem related to the bending creep characteristic KANTO JIDOSHA KOGYO KABUSHIKI KAISHA, a co-applicant of the present application, proposed a method for precisely analyzing the bending creep characteristic by multiplying the tensile creep or compressive creep after heating, obtained as a result of an analysis using Nutting's formula, by an experimentally determined correction coefficient (Japanese Patent Application No. Hei 9-352189).

SUMMARY OF THE INVENTION

One object of the method for analyzing thermal deformation according to the present invention is to precisely analyze the thermal deformation of a substance which thermally shrinks over time.

In order to achieve at least the object mentioned above, the thermal deformation analysis according to the present invention employs the following method.

According to one aspect of the present invention, there is provided a thermal deformation analysis method for analyzing thermal deformation of a substance in which deformation occurs in response to an increase and the following decrease in temperature, and while the temperature increases and then decreases over time, wherein thermal deformation of the substance is analyzed based on a creep characteristic which relates to the creep deformation of the substance occurring during the temperature increase and the following temperature decrease as time elapses, and a thermal shrinkage characteristic which relates to the thermal shrinkage deformation of the substance occurring during the temperature increase and the following temperature decrease as time elapses.

In this aspect of the thermal deformation analysis method, thermal deformation of the substance is analyzed based on the creep characteristic which relates to the creep deformation of the substance occurring during the temperature increase and the following temperature decrease as time elapses, and the thermal shrinkage characteristic which relates to the thermal shrinkage deformation of the substance occurring during the temperature increase and the following temperature decrease as time elapses. As a result, analysis can be more precisely performed compared to an analysis of the conventional method which does not take thermal shrinkage characteristic into account.

It is also preferable to configure the thermal deformation analysis method to comprise a calculation step for deformation during temperature increase, for calculating the elasto-plastic deformation of the substance during the process of raising the temperature of the substance to a predetermined temperature, based on the elasto-plastic characteristic of the substance; a calculation step for creep deformation, for calculating the creep deformation of the substance when the substance is exposed to the predetermined temperature environment for a predetermined period of time, based on the creep characteristic; and a calculation step for deformation during the following temperature decrease, for calculating the elasto-plastic deformation of the substance during the process of cooling the substance from the elevated temperature to a predetermined low temperature, based on the elasto-plastic characteristic of the substance, wherein the thermal shrinkage characteristic is included in at least one of the three steps in calculating the deformation of the substance. In this manner, the deformation of the substance can be analyzed from the elasto-plastic deformation, creep deformation, and thermal shrinkage deformation, during a temperature increase and the following temperature decrease.

In the aspect of the thermal deformation analysis method of the present invention comprising the above three steps, it is also preferable that the creep deformation calculation step is a step for calculating the deformation by taking the sum of the deformation produced by the creep strain obtained from the creep characteristic with respect to time and the deformation produced by the thermal shrinkage obtained based on the thermal shrinkage characteristic with respect to time as the total deformation with respect to time of said substance. In such a case, in the calculation, the thermal shrinkage deformation occurring as time elapses is assumed to be simultaneous with the creep deformation.

Further, in the aspect of the thermal deformation analysis method of the present invention comprising the above three steps, it is also preferable that the calculation step for deformation during temperature increase is a step for calculating the elasto-plastic deformation of the substance based on the linear expansion coefficient of the substance obtained according to the elasto-plastic deformation characteristic and on the thermal shrinkage rate of the substance obtained according to the thermal shrinkage characteristic. In such a case, in the calculation, the thermal shrinkage deformation occurring as time elapses is assumed to be simultaneous with the elasto-plastic deformation during the temperature increase. Because the saturated amount of thermal shrinkage is calculated during temperature increase process, this is especially effective when the thermal shrinkage is saturated or nearly saturated at an early stage of the temperature increase.

Still further, in the aspect of the thermal deformation analysis method of the present invention comprising the above three steps, it is also preferable that the calculation step for deformation during the following temperature decrease is a step for calculating the elasto-plastic deformation of the substance based on the linear expansion coefficient of the substance obtained according to the elasto-plastic deformation characteristic and on the thermal shrinkage rate of the substance obtained according to the thermal shrinkage characteristic. In such a case, in the calculation, the thermal shrinkage deformation occurring as time elapses is assumed to be simultaneous with the elasto-plastic deformation during the temperature decrease.

DESCRIPTION OF THE PREFERRED EMBODIMENTS

Figure 1:
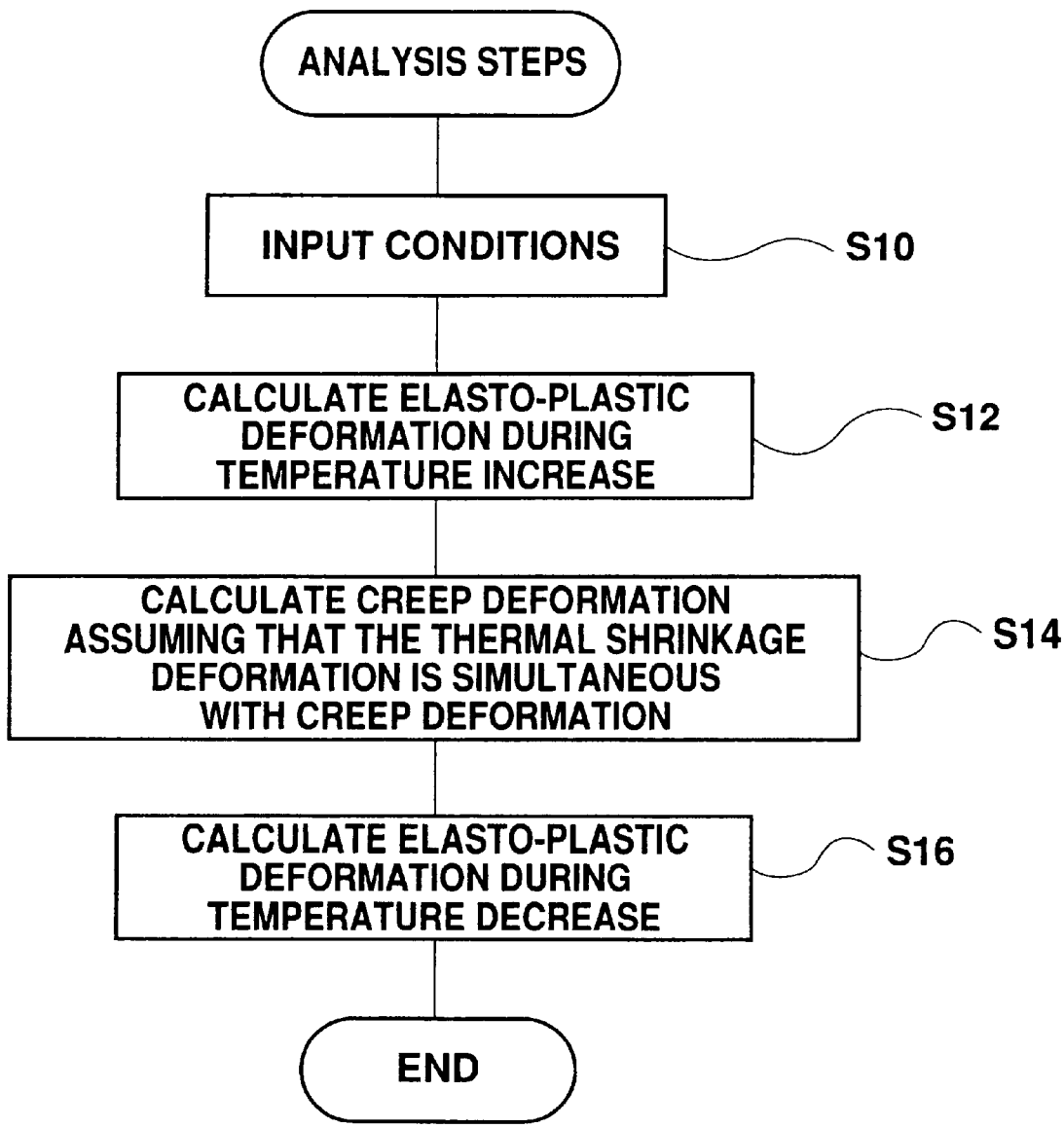
FIG. 1 is a diagram schematically showing the analysis step of a method for analyzing thermal deformation of a first embodiment of the present invention.

The preferred embodiments of the present invention will now be described. FIG. 1 is a diagram schematically showing the analysis steps of the method for analyzing thermal deformation according to the first embodiment of the present invention. As shown in FIG. 1, in this method for analyzing thermal deformation, the necessary data for analysis by using the finite element method, such as linear expansion coefficient, Young's modulus, Poisson's ratio, shape, and constraint condition of the substance, which is the analysis target, are input (step S10). Then, the elasto-plastic deformation during temperature increase is calculated (step S12). The creep deformation is calculated from strain rate which includes thermal shrinkage, based on an assumption that the thermal shrinkage deformation occurs simultaneously with the creep deformation (step S14). Then, the elasto-plastic deformation during the temperature decrease is calculated (step S16), and the analysis is completed.

The strain rate used in the calculation of the creep deformation at step S14 is determined as follows. First, as shown in Equation (2), a total strain $\epsilon$ for representing the creep deformation and thermal shrinkage deformation behaviors, is considered to be the sum of the creep strain $\epsilon_{cr}$ ($\sigma$, t, . . . ) which is a function of at least time t and stress $\sigma$, and the thermal shrinkage rate $\alpha(t)$ which is a function of time t.

ti $\epsilon = \epsilon_{cr}(\sigma, t, \ldots) + \alpha(t) + $tm (2)

In this equation, $\sigma$ represents stress, t represents elapsed time, and . . . represents other variables.

The strain rate can be obtained from the time derivative of the total strain, as shown in Equation (3). Using the form of Nutting's formula of Equation 1 for the creep strain $\epsilon_{cr}$ ($\sigma$, t, . . . ), the equation for strain rate is expressed as Equation (4).

$$\frac{\partial \varepsilon}{\partial t} = \frac{\partial (\varepsilon_{cr}(\sigma, t, \cdots) + \alpha(+))}{\partial t} \qquad (3)$$

$$\frac{\partial \varepsilon}{\partial t} = A\sigma^n t^m + \frac{d\alpha(t)}{dt} \qquad (4)$$

Therefore, the calculation of creep deformation at step S14 can be performed by integrating the strain rate over the time from when the temperature increase is started to when the following temperature decrease is completed.

The thermal shrinkage deformation is calculated along with the creep deformation as described above, for it is assumed that the thermal shrinkage occurring over time is simultaneous with the creep deformation.

The calculation of elasto-plastic deformation during the temperature increase of step S12 can be performed by multiplying the linear expansion coefficient $\beta$ of the substance by the temperature difference during the temperature increase (difference between the temperature T2 after the temperature increase and temperature T1 before the temperature increase). The calculation of the elasto-plastic deformation during the temperature decrease of step S16 can be performed by multiplying the linear expansion coefficient $\beta$ of the substance by the temperature difference during the temperature decrease (difference between the temperature T3 after the temperature decrease and the temperature T2 before the temperature decrease).

Figure 2:
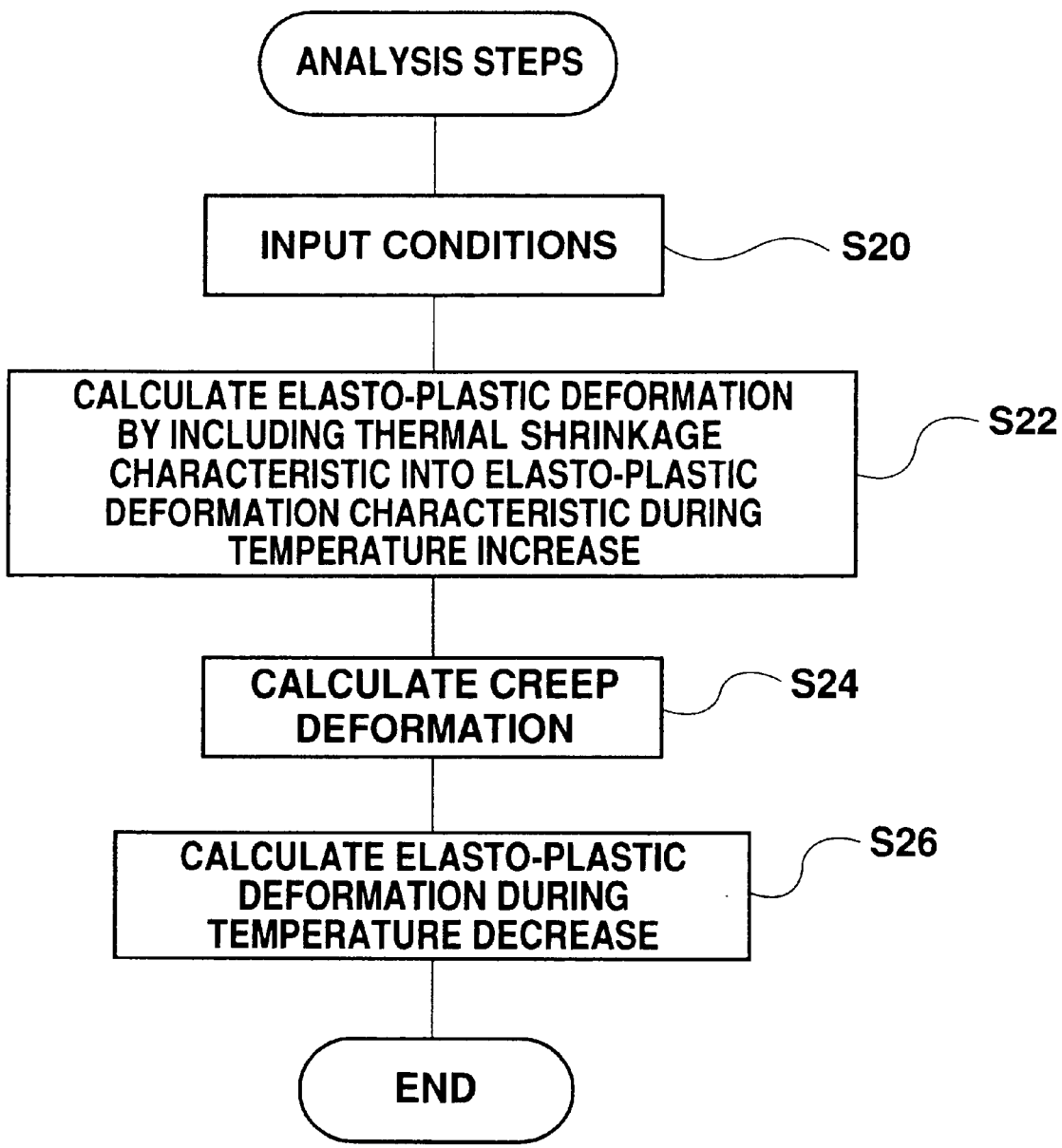
FIG. 2 is a diagram schematically showing the analysis step of a method for analyzing thermal deformation of a second embodiment of the present invention.

Next, a method for analyzing thermal deformation according to the second embodiment of the present invention will be described. FIG. 2 is a diagram schematically showing the analysis step according to the second embodiment. In the method for analyzing thermal deformation according to the second embodiment, the necessary data for analysis by using the finite element method are first input (step S20), similar as in the method for analyzing thermal deformation according to the first embodiment. Then, the elasto-plastic deformation during the temperature increase is calculated, with the thermal shrinkage characteristic included in the elasto-plastic deformation characteristic during the temperature increase (step S22). After that, the creep deformation of the substance is then calculated (step S24), and the elasto-plastic deformation during the temperature decrease is calculated (step S26). The analysis is then completed.

The calculation of the elasto-plastic deformation during the temperature increase of step S22 is performed using an apparent linear expansion coefficient β1 obtained by including thermal shrinkage into linear expansion. The apparent linear expansion coefficient β1 can be obtained by adding, to the linear expansion coefficient β of the substance, a value obtained by dividing the thermal shrinkage rate α1 by the temperature difference during the temperature increase (difference between the temperature T2 after the temperature increase and the temperature T1 before the temperature increase), as shown by Equation (5).

$$\beta1=\beta+\alpha1/(T2-T1) \qquad (5)$$

Thus, the calculation of the elasto-plastic deformation during the temperature increase of step S22 can be performed using the apparent linear expansion coefficient β1 obtained as above.

The calculation of the creep deformation of step S24 can be performed by integrating the change of creep strain $\epsilon_{cr}(\sigma, t, \ldots)$ over time as described above, that is, the strain rate from the completion of the temperature increase till the start of the temperature decrease. Here, the Nutting's formula of equation (1) can be used.

The calculation of the elasto-plastic deformation during the temperature decrease of step S26 can be performed using the linear expansion coefficient β of the substance and the temperature difference during the temperature decrease (difference between the temperature T3 after the temperature decrease and the temperature T2 before the temperature decrease), similar to the method for analyzing thermal deformation of the first embodiment.

The method for analyzing thermal deformation of embodiment 2 can be applied to a case where the thermal shrinkage deformation is saturated or nearly saturated at the early stage of the temperature increase. This is because, in the calculation, the thermal shrinkage is only present during the temperature increase.

Figure 3:
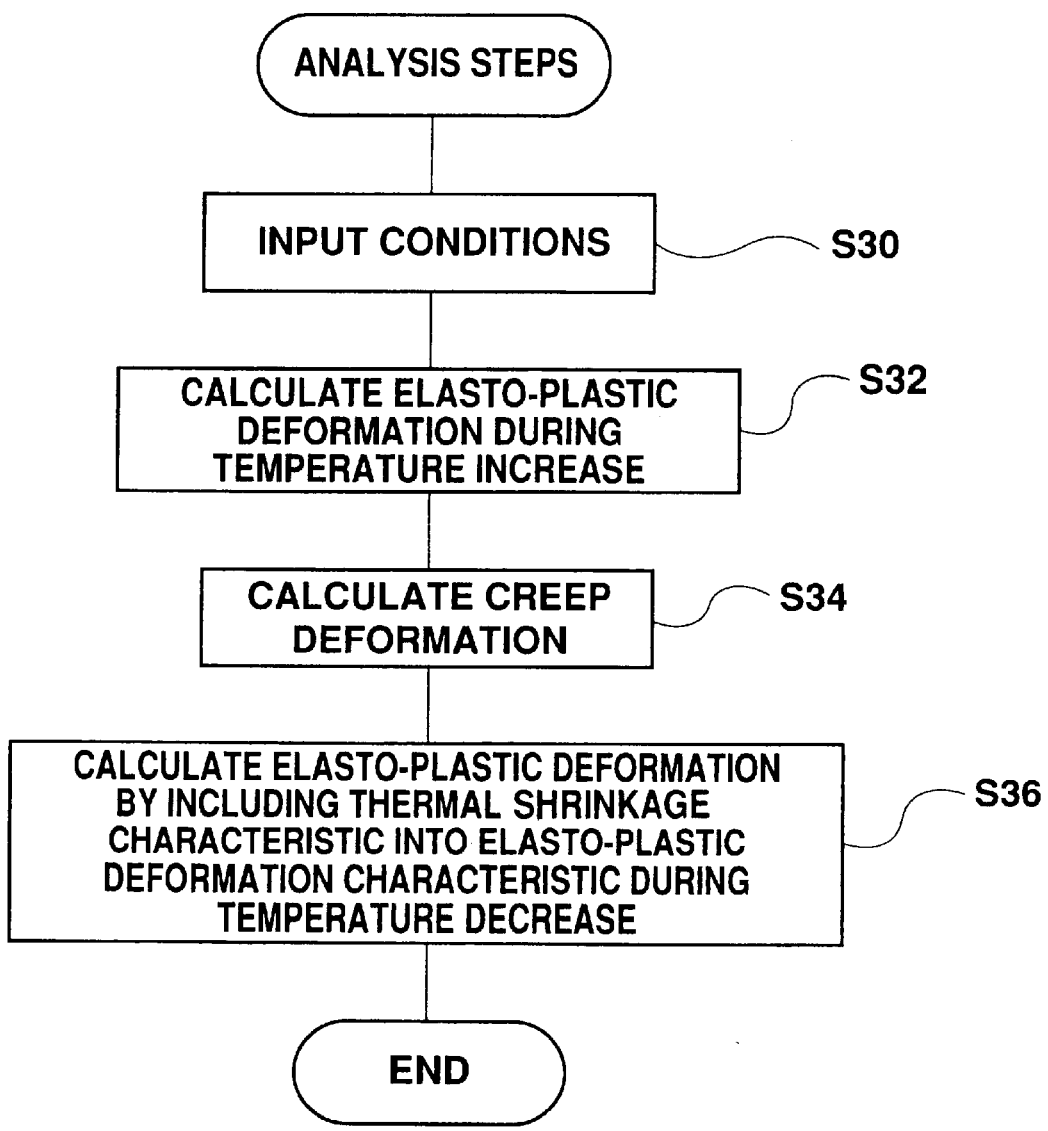
FIG. 3 is a diagram schematically showing the analysis step of a method for analyzing thermal deformation of a third embodiment of the present invention.

A method for analyzing thermal deformation according to a third embodiment of the present invention will now be described. FIG. 3 is a diagram schematically showing the analysis step of a method of analyzing thermal deformation according to the third embodiment of the present invention. As shown in FIG. 3, in this method for analyzing thermal deformation of the third embodiment, the necessary data for analysis by using the finite element method is first input (step S30), similar as in the method for analyzing thermal deformation of the first embodiment described above. Then, the elasto-plastic deformation during the temperature increase is calculated (step S32). The creep deformation of the substance is calculated (step S34), and the elasto-plastic deformation during the temperature decrease is calculated by including the thermal shrinkage characteristic into the elasto-plastic deformation characteristic during the temperature decrease (step S36). The analysis is then completed.

The calculation of the elasto-plastic deformation during the temperature increase at step S32 is similar to the calculation of the elasto-plastic deformation during the temperature increase at step S12 of the method for analyzing thermal deformation of the first embodiment. The calculation of the creep deformation at step S34 is similar to the calculation of the creep deformation at step S24 of the method of analyzing thermal deformation of the second embodiment.

The calculation of the elasto-plastic deformation during the temperature decrease at step S36 is performed using an apparent linear expansion coefficient β2 obtained by including thermal shrinkage into linear expansion. The apparent linear expansion coefficient β2 can be obtained by adding, to the linear expansion coefficient β, a value obtained by dividing the thermal shrinkage rate α2 by the temperature difference during the temperature decrease (difference between the temperature T3 after the temperature decrease and the temperature T2 before the temperature decrease), as shown in Equation (6).

$$\beta2=\beta+\alpha2/(T2-T3) \qquad (6)$$

Therefore, the calculation of the elasto-plastic deformation during the temperature decrease at step S36 can be performed using the apparent linear expansion coefficient β2 obtained in this manner. In the method of analyzing thermal deformation of the third embodiment, the thermal shrinkage deformation is performed simply during the temperature decrease.

Figure 4:
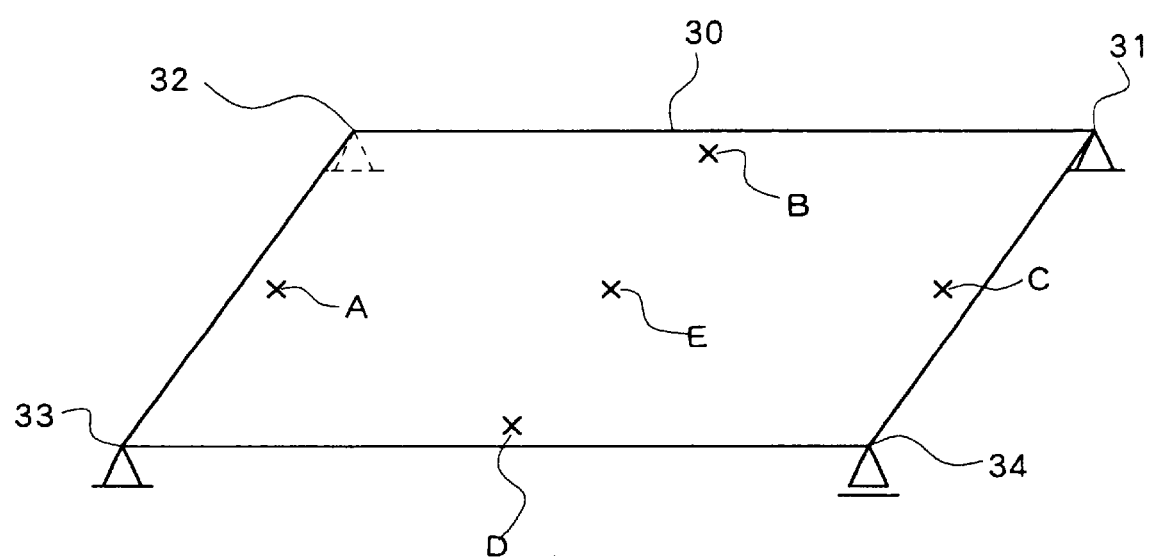
FIG. 4 is a diagram showing a model of a bending rectangular plate specimen 30.
Figure 5:
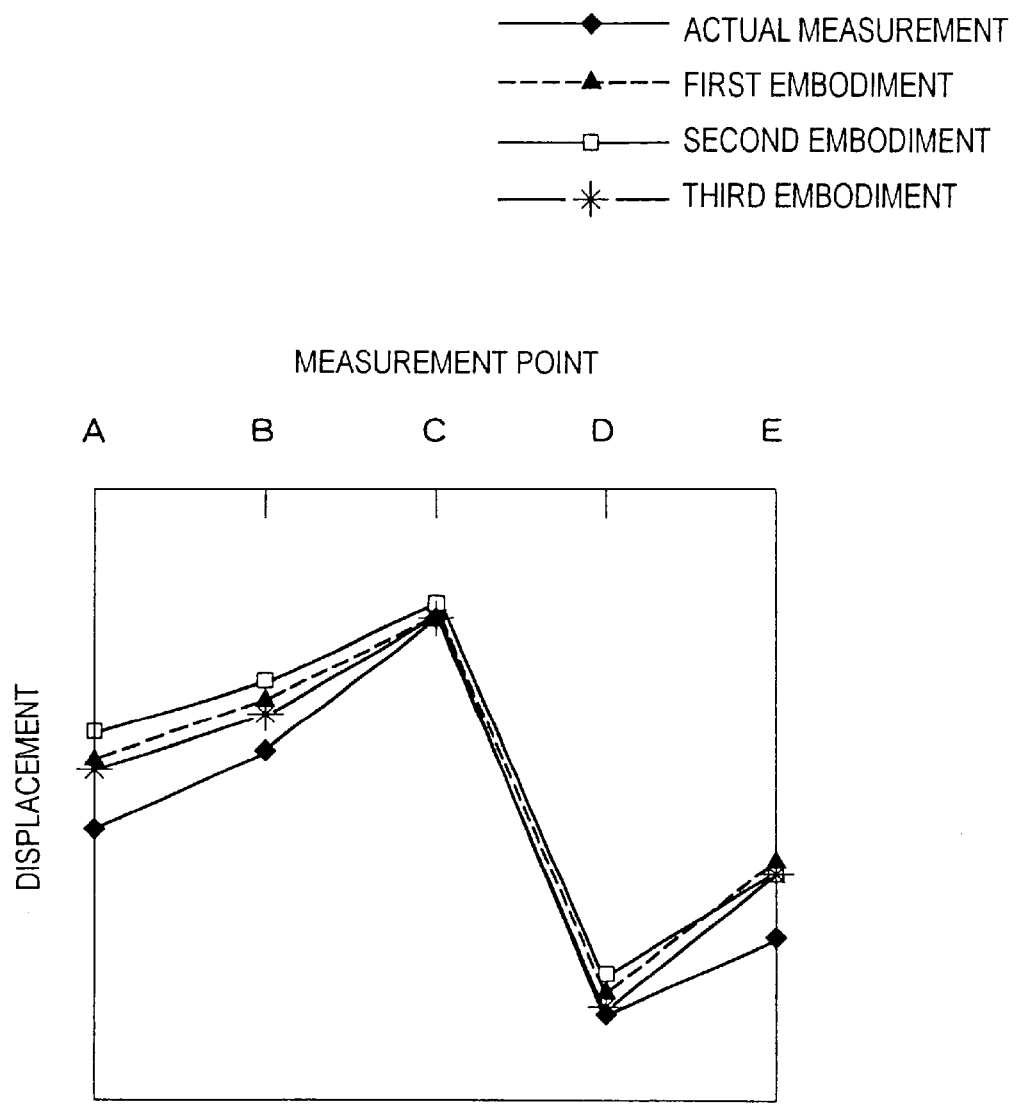
FIG. 5 is a diagram for comparing the experimentally measured deformation of a rectangular plate specimen 30 after a heat resistance test and the analysis results obtained by thermal deformation analysis according to the first through the third embodiments.

The precision of analysis by the methods for analyzing thermal deformation of the first through the third embodiments will now be compared. FIG. 4 is a diagram showing a model and constraint condition of a rectangular plate specimen 30 for a heat resistance test. The plate specimen 30 is injection molded from a polypropylene. FIG. 5 is a diagram for comparing the experimentally measured deformation of a rectangular plate specimen 30 after a heat resistance test and the analysis results obtained by the methods for analyzing thermal deformation of the first through the third embodiment. As shown in FIG. 4, three corners (31–33) among the four corners in the rectangular plate specimen 30 are completely fixed and the remaining corner (34) is supported by a hinge which can move horizontally. Five "x"s (A through E) shown on the rectangular specimen 30 in FIG. 4 represent the measurement points for measuring the amount of displacement.

As shown in FIG. 5, all of the analysis results obtained by the methods for analyzing thermal deformation of the first through the third embodiments well coincide with the actual measurements.

Figure 6:
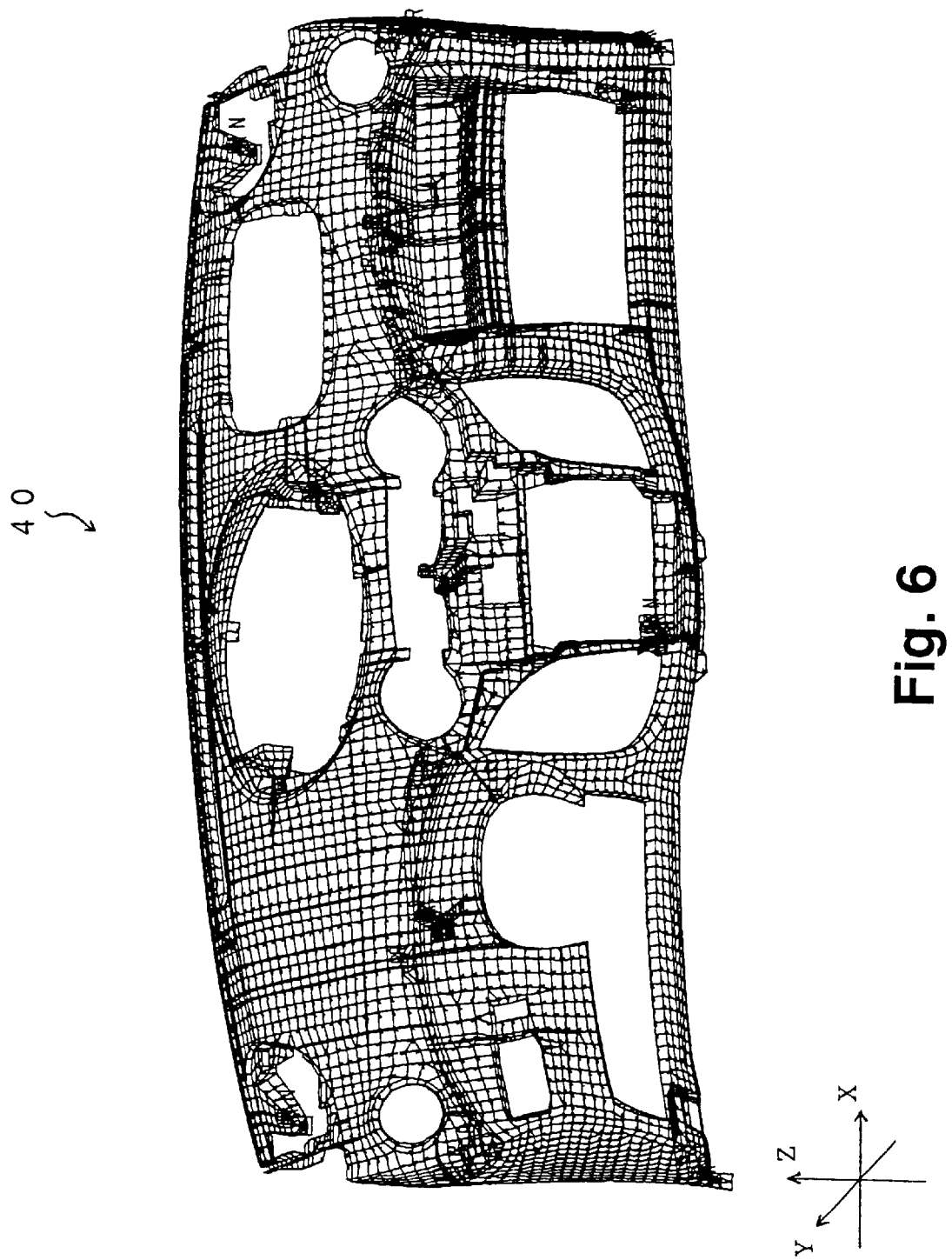
FIG. 6 is a diagram showing the appearance of an instrument panel 40 of a vehicle, injection molded from a polypropylene.
Figure 7:
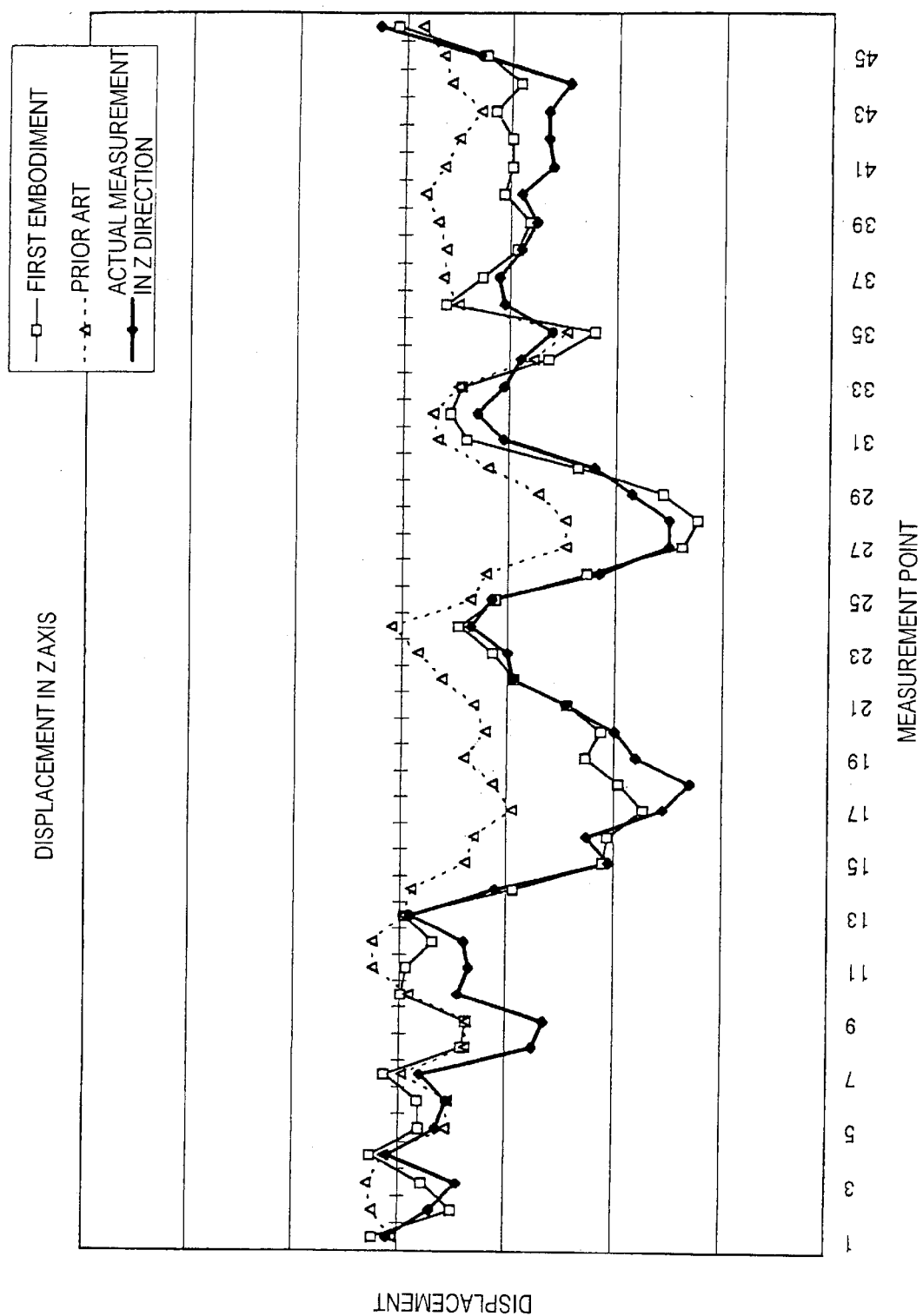
FIG. 7 is a diagram for comparing the measured values of the displacement in the z direction of FIG. 6 at each measurement point on the instrument panel 40 after experienced a heat resistance test, the analysis result obtained by using the method for analyzing thermal deformation of the first embodiment, and analysis results obtained by using a conventional method for analyzing deformation which does not take the thermal shrinkage into account.
Figure 8:
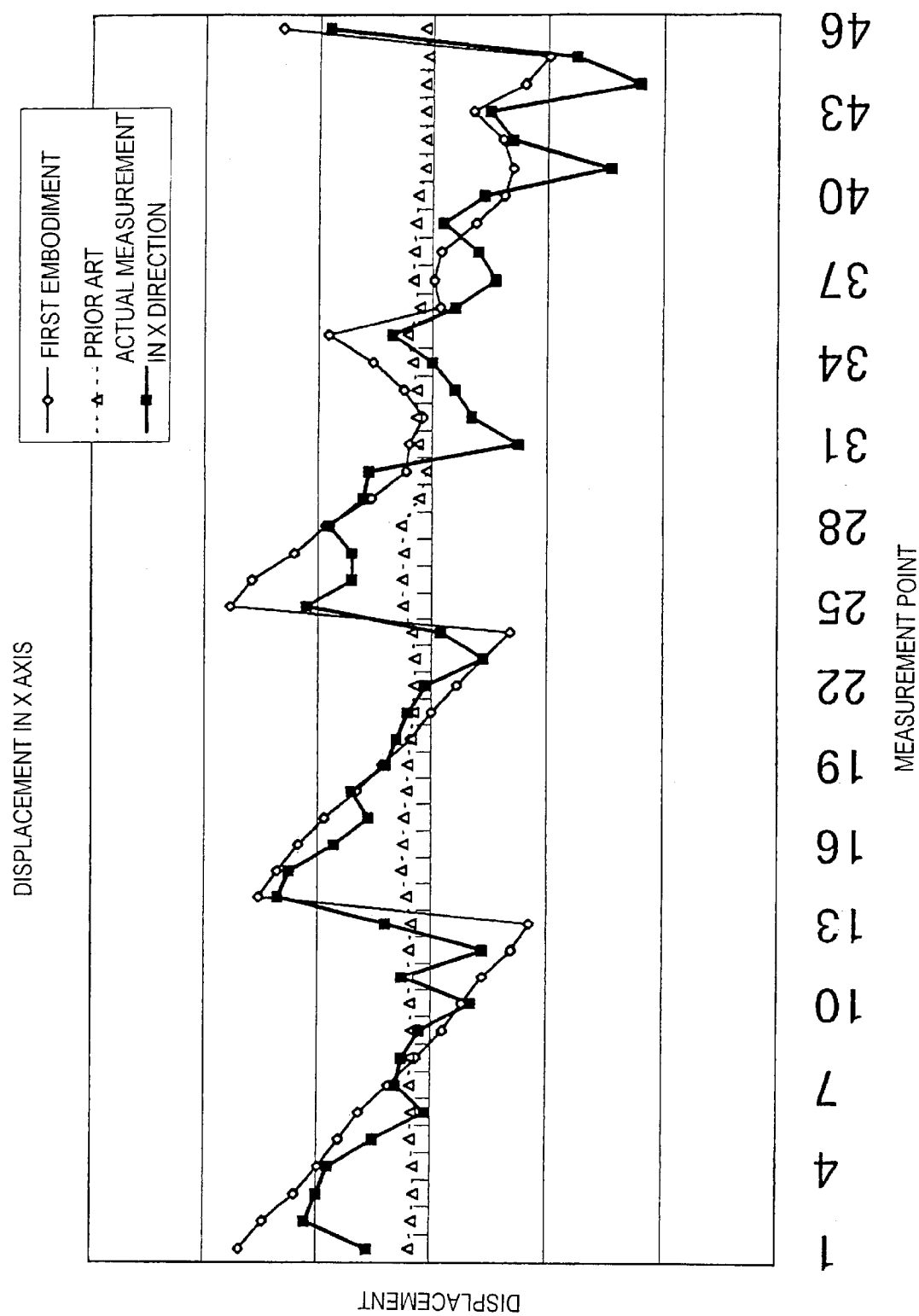
FIG. 8 is a diagram for comparing the measured values of the displacement in the x direction in FIG. 6 at each measurement point on the instrument panel 40 after experienced a heat resistance test, the analysis results obtained by the method for analyzing thermal deformation of the first embodiment, and analysis results obtained by using a conventional method for analyzing deformation which does not take the thermal shrinkage into account.

FIG. 6 is a diagram showing the appearance of an instrument panel 40 of a vehicle, injection molded from a polypropylene. FIG. 7 is a diagram for comparing the measured values of the displacement in the z direction as shown in FIG. 6 at each measurement point on the instrument panel 40 after experienced a heat resistance test, the analysis results obtained by using the method for analyzing thermal deformation of the first embodiment, and the analysis results obtained by using a method for analyzing deformation which does not take the thermal shrinkage into account. FIG. 8 is a diagram for comparing the measured value of the displacement in the x direction of FIG. 6 at each measurement point on the instrument panel 40 after experienced a heat resistance test, the analysis results obtained by using the method for analyzing thermal deformation of the first embodiment, and the analysis results obtained by using a method for analyzing deformation which does not take the thermal shrinkage into account. Although not shown in FIG. 6, 45 measurement points are provided on the instrument panel 40.

As is clear from FIGS. 7 and 8, the results of analysis using the method for analyzing thermal deformation of the first embodiment more precisely coincide with the actual measurements than do the results obtained using a conventional method for analyzing deformation.

According to the method for analyzing thermal deformation of the first through the third embodiments, thermal deformation of the substance can be analyzed with high precision. In the method of the first embodiment, the thermal deformation of the substance can be analyzed with high precision by calculating the creep deformation from the strain rate which includes the thermal shrinkage, by assuming that the thermal shrinkage deformation of the substance occurs simultaneous with the creep deformation. In the second embodiment, the thermal deformation of the substance can be analyzed with high precision by calculating the elasto-plastic deformation during the temperature increase using an apparent linear expansion coefficient $\beta1$ obtained by including thermal shrinkage into linear expansion. In the third embodiment, the thermal deformation of the substance can be analyzed with high precision by calculating the elasto-plastic deformation during the temperature decrease using an apparent linear expansion coefficient $\beta2$ obtained by including thermal shrinkage into linear expansion.

According to an experiment performed by the present applicant, the analysis time required for the method of analyzing thermal deformation of the first embodiment is about 1.5 times the analysis time required for the methods for analyzing thermal deformation of the second and third embodiments. Therefore, analysis can be performed more quickly by employing the method for analyzing thermal deformation of the second or the third embodiment.

In the above description of the precision of the method for analyzing thermal deformation of each embodiment, the method for analyzing thermal deformation of each embodiment is applied to an example of a substance such as a rectangular specimen 30 and instrument panel 40 which are injection molded from a polypropylene. However, it is also possible to apply the method for analyzing thermal deformation of each embodiment when analyzing thermal deformation of any substance formed by any resin such as, for example, polyethylene, polystyrene, or ABS, or any other material which thermally expand or shrink as time elapses.

In the method for analyzing thermal deformation of each embodiment, the calculation is performed by using the finite element method. However, the calculation may also be performed by a method other than the finite element method.

The preferred embodiments of the present invention have been described. However, the present invention is not limited to these embodiments, and it should be understood that the present invention can be realized in various forms without departing from the scope of the present invention.

What is claimed is:

1. A thermal deformation analysis method for analyzing thermal deformation of a substance in which deformation occurs in response to an increase and the following decrease in temperature, and while the temperature increases or decreases over time, wherein thermal deformation of the substance is analyzed based on a creep characteristic which relates to the creep deformation of said substance occurring during said temperature increase or decrease as time elapses, and a thermal shrinkage characteristic which relates to the thermal shrinkage deformation of said substance occurring during said temperature increase or decrease as time elapses, the method comprising the steps of:

a calculation step for deformation during temperature increase, for calculating the elasto-plastic deformation of the substance during the temperature increase of said substance to a predetermined temperature, based on the elasto-plastic deformation characteristic of the substance;

a calculation step for creep deformation, for calculating the creep deformation of the substance when said substance is exposed to said predetermined temperature for a predetermined period of time, based on said creep characteristic; and a calculation step for deformation during the following temperature decrease, for calculating the elasto-plastic deformation of the substance during the temperature decrease of said substance from said predetermined temperature, based on the elasto-plastic deformation characteristic of the substance; wherein the calculation step for deformation during temperature increase, the calculation step for creep deformation, or the calculation step for deformation during the following temperature decrease, is conducted based on said thermal shrinkage characteristic.

2. A thermal deformation analysis method according to claim 1 wherein said creep deformation calculation step is a step for calculating the deformation by taking the sum of the deformation produced by the creep strain obtained from the creep characteristic with respect to time and the deformation produced by the thermal shrinkage obtained based on the thermal shrinkage characteristic with respect to time as the total deformation with respect to time of said substance.

3. A thermal deformation analysis method according to claim 1, wherein said calculation step for deformation during temperature increase is a step for calculating the elasto-plastic deformation of the substance based on the linear expansion coefficient of said substance obtained according to said elasto-plastic deformation characteristic and the thermal shrinkage rate of the substance obtained according to said thermal shrinkage characteristic.

4. A thermal deformation analysis method according to claim 1, wherein said calculation step for deformation during temperature decrease is a step for calculating the elasto-plastic deformation of the substance based on the linear expansion coefficient of said substance obtained according to said elasto-plastic deformation characteristic and the thermal shrinkage rate of the substance obtained according to said thermal shrinkage characteristic.

* * * * *